US012016535B2

(12) United States Patent
Yan et al.

(10) Patent No.: US 12,016,535 B2
(45) Date of Patent: Jun. 25, 2024

(54) FLEXIBLE TUBE-BASED DETECTION AND PACKAGING STRUCTURE AND IN-VIVO DETECTION DEVICE

(71) Applicant: INNOVEX MEDICAL CO., LTD, Shanghai (CN)

(72) Inventors: Hang Yan, Shanghai (CN); Wei Tang, Shanghai (CN); Ruifeng Gao, Shanghai (CN); Zimei Zhang, Shanghai (CN)

(73) Assignee: INNOVEX MEDICAL CO., LTD, Shanghai (CN)

( * ) Notice: Subject to any disclaimer, the term of this patent is extended or adjusted under 35 U.S.C. 154(b) by 330 days.

(21) Appl. No.: 17/049,951

(22) PCT Filed: Jan. 29, 2019

(86) PCT No.: PCT/CN2019/073614
§ 371 (c)(1),
(2) Date: Oct. 22, 2020

(87) PCT Pub. No.: WO2020/124752
PCT Pub. Date: Jun. 25, 2020

(65) Prior Publication Data
US 2021/0353134 A1    Nov. 18, 2021

(30) Foreign Application Priority Data
Dec. 21, 2018   (CN) .......................... 201811570625.6

(51) Int. Cl.
*A61B 1/06*    (2006.01)
*A61B 1/00*    (2006.01)
(Continued)

(52) U.S. Cl.
CPC ........ *A61B 1/0676* (2013.01); *A61B 1/00018* (2013.01); *A61B 1/0008* (2013.01);
(Continued)

(58) Field of Classification Search
CPC ............ A61B 1/00091; A61B 1/00094; A61B 1/00119; A61B 1/00137; A61B 1/018; A61B 1/05; A61B 1/051; A61B 1/053
See application file for complete search history.

(56) References Cited

U.S. PATENT DOCUMENTS 5,040,069 A * 8/1991 Matsumoto ............ H04N 23/54
348/340
6,635,865 B1 * 10/2003 Soltyk ................ H04N 1/02805
250/239

(Continued)

OTHER PUBLICATIONS

PCT/CN2019/073614 International Search Report dated Sep. 12, 2019 and English translation.

*Primary Examiner* — Aaron B Fairchild
*Assistant Examiner* — Stephen Floyd London
(74) *Attorney, Agent, or Firm* — NZ CARR LAW OFFICE

(57) ABSTRACT

The present invention provides a detection packaging structure and an in-vivo detection apparatus that are based on a flexible tube. A detection circuit board and a main circuit board that are perpendicular to each other are used, a first conducting material is disposed on a first side surface of the detection circuit board, a second conducting material capable of being conducted to the first conducting material is disposed on a second side surface, and when a detection component is connected to the first side surface of the detection circuit board, a wiring terminal of the detection component is capable of being welded to the first conducting material. In this way, based on the present invention, difficulty of welding operations is reduced, welding strength and reliability are enhanced, and welding stability in a plurality of motion statuses is satisfied. Based on the present invention, stable mounting and use of the detection component are further ensured through assembly of the main circuit board (Continued)

and the detection circuit board, so that the detection component is not impacted by external force. In addition, the detection circuit board is perpendicularly disposed on a first side surface of the main circuit board, which helps rationalize space utilization, thereby facilitating reduction of an overall size of the structure.

18 Claims, 6 Drawing Sheets

(51) Int. Cl.
    *A61B 1/005*     (2006.01)
    *A61B 1/018*     (2006.01)
    *A61B 1/05*     (2006.01)
    *H05K 1/14*     (2006.01)
    *H05K 1/18*     (2006.01)

(52) U.S. Cl.
    CPC ........ *A61B 1/00096* (2013.01); *A61B 1/0011* (2013.01); *A61B 1/018* (2013.01); *A61B 1/05* (2013.01); *H05K 1/141* (2013.01); *H05K 1/181* (2013.01); *A61B 1/005* (2013.01); *A61B 2560/04* (2013.01); *A61B 2562/02* (2013.01); *A61B 2562/223* (2013.01); *A61B 2562/227* (2013.01); *H05K 2201/10151* (2013.01)

(56) References Cited

U.S. PATENT DOCUMENTS

| | | | |
|---|---|---|---|
| 7,927,548 B2 | 4/2011 | Slowey | |
| 9,814,393 B1 | 11/2017 | Mao et al. | |
| 2015/0271370 A1* | 9/2015 | Henley | H04N 23/54 |
| | | | 348/76 |
| 2015/0378144 A1* | 12/2015 | Handte | A61B 1/00131 |
| | | | 250/208.1 |
| 2017/0064249 A1* | 3/2017 | Kitano | A61B 1/051 |
| 2017/0224203 A1* | 8/2017 | Tanahashi | H05K 1/111 |
| 2017/0251914 A1* | 9/2017 | Kitano | A61B 1/128 |
| 2020/0192078 A1* | 6/2020 | Spring | A61B 1/051 |
| 2020/0194951 A1* | 6/2020 | Loo | H05K 3/3405 |
| 2020/0196434 A1* | 6/2020 | Kuo | H04N 23/57 |
| 2021/0290041 A1* | 9/2021 | Morita | A61B 1/00087 |

\* cited by examiner

FLEXIBLE TUBE-BASED DETECTION AND PACKAGING STRUCTURE AND IN-VIVO DETECTION DEVICE

TECHNICAL FIELD

The present invention relates to the medical field, and in particular, to a detection packaging structure and an in-vivo detection apparatus that are based on a flexible tube.

BACKGROUND ART

With development of science and technologies, in-vivo detection technologies based on flexible tubes have been widely applied to the medical field. An in-vivo detection apparatus based on a flexible tube can be extended into a human body to help medical personnel inspect an internal organ of the human body.

In the related art, the in-vivo detection apparatus based on the flexible tube may include a flexible controllable curved tube and a detection component formed at an end of the controllable curved tube. A wiring terminal of the detection component may be welded to another cable through welding, to realize electrical transmission.

However, due to a relatively small size of the detection component and a relatively small size of a cable of the detection component, it is inconvenient to weld the detection component to another cable. In addition, it is difficult to ensure a welding effect during motion. For example, it is easy for the cable of the detection component to disconnect from another cable during motion.

SUMMARY

The present invention provides a detection packaging structure and an in-vivo detection apparatus that are based on a flexible tube, to resolve a problem of inconvenient operations during welding.

According to a first aspect of the present invention, a detection packaging structure based on a flexible tube is provided, including: a main circuit board, a detection circuit board, a detection component, an instrument tube, a tube cap, and an outer tube, where the detection circuit board is perpendicularly disposed on a first side surface, along a first direction, of the main circuit board, the instrument tube is disposed on a second side surface, along the first direction, of the main circuit board, and the detection component is disposed, along a second direction, on a first side surface of the detection circuit board; the tube cap is mounted on the second side surface of the main circuit board, and is connected to an end of the instrument tube;

a first conducting material is disposed on the first side surface, along the second direction, of the detection circuit board, a second conducting material capable of being conducted to the first conducting material is disposed on a second side surface, along the second direction, of the detection circuit board, a detection conducting material is disposed on the first side surface of the main circuit board, a wiring terminal of the detection component is conductively welded to the first conducting material, one end of the detection conducting material is conductively welded to the second conducting material, and the other end of the detection conducting material is conductively connected to a cable;

the main circuit board, the detection circuit board, the detection component, the tube cap, and a part of the instrument tube are all disposed in the outer tube, and the outer tube is directly or indirectly connected to a flexible controllable curved tube; and the first direction is perpendicular to the second direction.

Optionally, the detection conducting material includes at least two conductive portions, the conductive portions are along the second direction, and the at least two conductive portions are parallel to each other.

Optionally, the main circuit board is provided with a mounting locating groove, and both the detection circuit board and the tube cap are mounted in the mounting locating groove in an insertion manner.

Optionally, an end surface of an end, distal from the instrument tube, of the tube cap is provided with a first inclined surface, and an end surface, proximal to the tube cap, of the outer tube is provided with a second inclined surface whose angle matches an angle of the first inclined surface.

Optionally, the detection component is an image acquisition component; a lighting component is disposed at an end of the main circuit board, and both the lighting component and the detection component are along the second direction, and face a same direction.

Optionally, an opening groove is provided at the end of the main circuit board, and the lighting component is disposed in the opening groove.

Optionally, a lighting conducting material is further disposed on the first side surface and/or the second side surface of the main circuit board, the lighting conducting material is conductively welded to the lighting component, at least two lighting components are connected in parallel, and the lighting conducting material is conductively connected to the cable.

Optionally, the instrument tube and the tube cap are glued together, and the detection component and the main circuit board are glued together.

Optionally, an edge of a side, distal from the main circuit board, of the detection circuit board is arc-shaped, and the arc-shaped edge matches an inner surface of the outer tube.

According to a second aspect of the present invention, an in-vivo detection apparatus based on a flexible tube is provided, including the detection packaging structure based on the flexible tube and the flexible controllable curved tube in the first aspect and the optional solutions of the first aspect, where the detection packaging structure based on the flexible tube forms an insertion portion at an end of the controllable curved tube.

For the detection packaging structure and the in-vivo detection apparatus that are based on the flexible tube provided in the present invention, the detection circuit board and the main circuit board that are perpendicular to each other are used, the first conducting material is disposed on the first side surface of the detection circuit board, the second conducting material capable of being conducted to the first conducting material is disposed on the second side surface, and when the detection component is connected to the first side surface of the detection circuit board, the wiring terminal of the detection component is capable of being welded to the first conducting material. In this way, the cable is prevented from being directly welded to the detection component by using the main circuit board and the detection circuit board that are perpendicular to each other, and the conducting materials disposed on the detection circuit board. In addition, the detection component needs to be welded only to the first conducting material disposed on the first side surface, thereby helping enlarge a welding spot of the detection component. Therefore, based on the present invention, difficulty of welding operations is reduced, welding strength and reliability are enhanced, and welding stability in a plurality of motion statuses is satisfied.

Based on the present invention, stable mounting and use of the detection component are further ensured through assembly of the main circuit board and the detection circuit board, so that the detection component is not impacted by external force. In addition, the detection circuit board is perpendicularly disposed on the first side surface of the main circuit board, which helps rationalize space utilization, thereby facilitating reduction of an overall size of the structure.

In an optional solution of the present invention, the cable can be conductively connected by using the at least two conductive portions parallel to each other, which can facilitate a welding operation of a cable corresponding to a sensing component and help increase welding strength.

In an optional solution of the present invention, the mounting locating groove can help reduce a radial size after the detection circuit board and the main circuit board are mounted.

In an optional solution of the present invention, the insertion passability of the insertion portion is effectively improved by using the first inclined surface and the second inclined surface.

BRIEF DESCRIPTION OF THE DRAWINGS

To describe the technical solutions in the embodiments of the present invention or in the prior art more clearly, accompanying drawings required to describe the embodiments or the prior art are briefly described below. It is obvious that the accompanying drawings described below are only some embodiments of the present invention. It is apparent to those of ordinary skill in the art that other drawings may be further obtained based on the accompanying drawings without inventive effort.

DESCRIPTION OF REFERENCE SIGNS

1—main circuit board;
11—detection conducting material;
12—first lighting conducting material;
13—second lighting conducting material;
14—opening groove;
15—mounting locating groove;
2—detection circuit board;
21—second conducting material;
3—detection component;
4—instrument tube;
5—tube cap;
6—lighting component; and
7—outer tube.

DETAILED DESCRIPTION

Technical solutions in the embodiments of the present invention are clearly and completely described below with reference to accompanying drawings in the embodiments of the present invention. Apparently, the described embodiments are only some rather than all of the embodiments of the present invention. Based on the embodiments of the present invention, all other embodiments obtained by those of ordinary skill in the art without creative efforts shall fall within the protection scope of the present invention.

Terms "first", "second", "third", "fourth", and the like (if any) in the specification and claims of the present invention and the foregoing accompanying drawings are used to distinguish similar objects, but do not need to be used for describing a specific sequence or an order. It should be understood that data used in this way can be interchanged under appropriate circumstances, so that the embodiments of the present invention described herein can be implemented in an order other than those illustrated or described herein. In addition, terms "including", "having", and any variations thereof are intended to cover non-exclusive inclusions, for example, processes, methods, systems, products, or devices that contain a series of steps or units need not be limited to those clearly listed steps or units, but may include other steps or units not explicitly listed or inherent to these processes, methods, products, or devices.

The technical solutions of the present invention are described in detail below with reference to the specific embodiments. The following several embodiments may be combined with each other, and a same or similar concept or process may not be described again in some embodiments.

Figure 1:
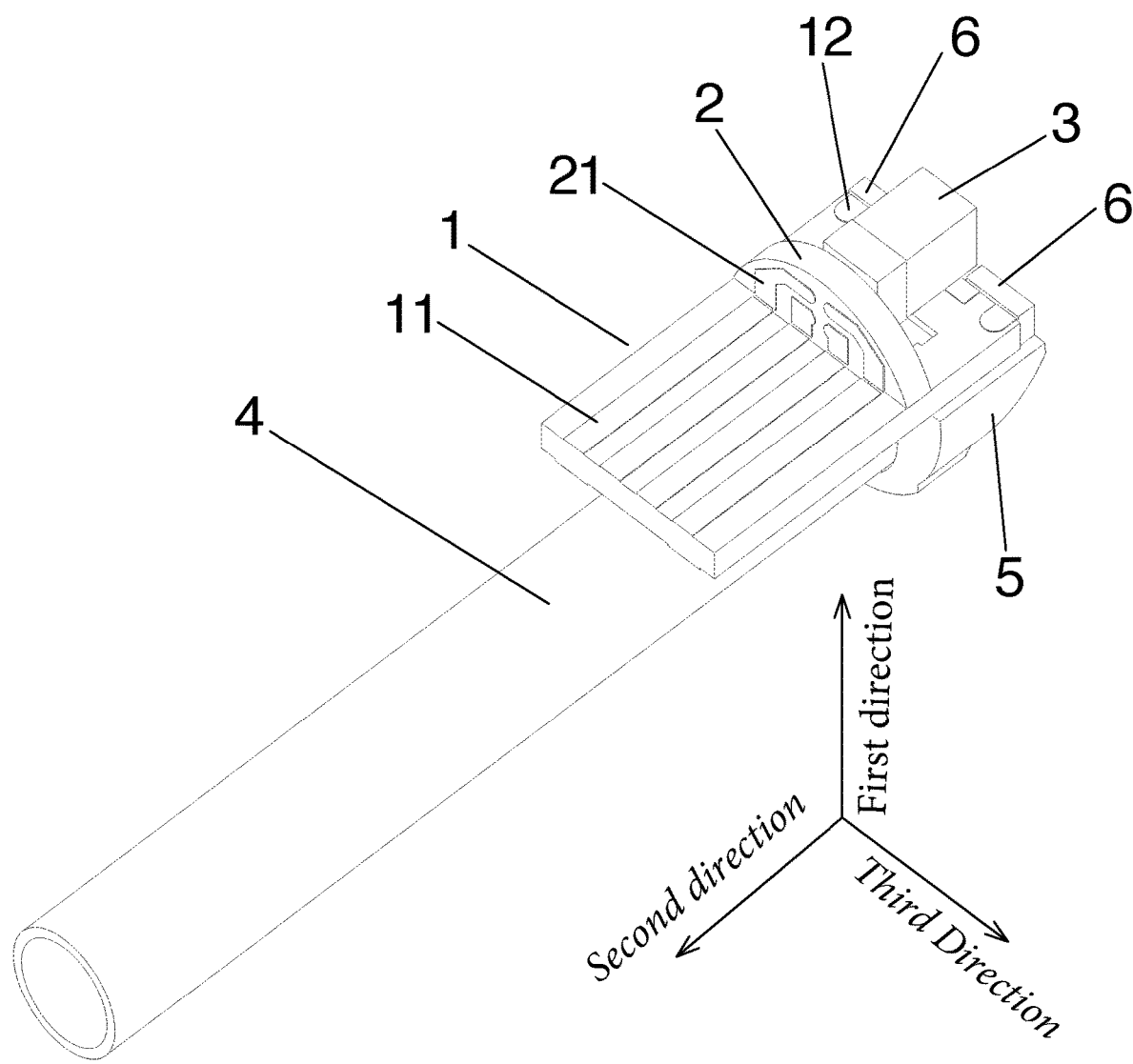
FIG. 1 is a schematic structural diagram 1 of a part of a detection packaging structure based on a flexible tube except an outer tube according to an embodiment of the present invention.
Figure 2:
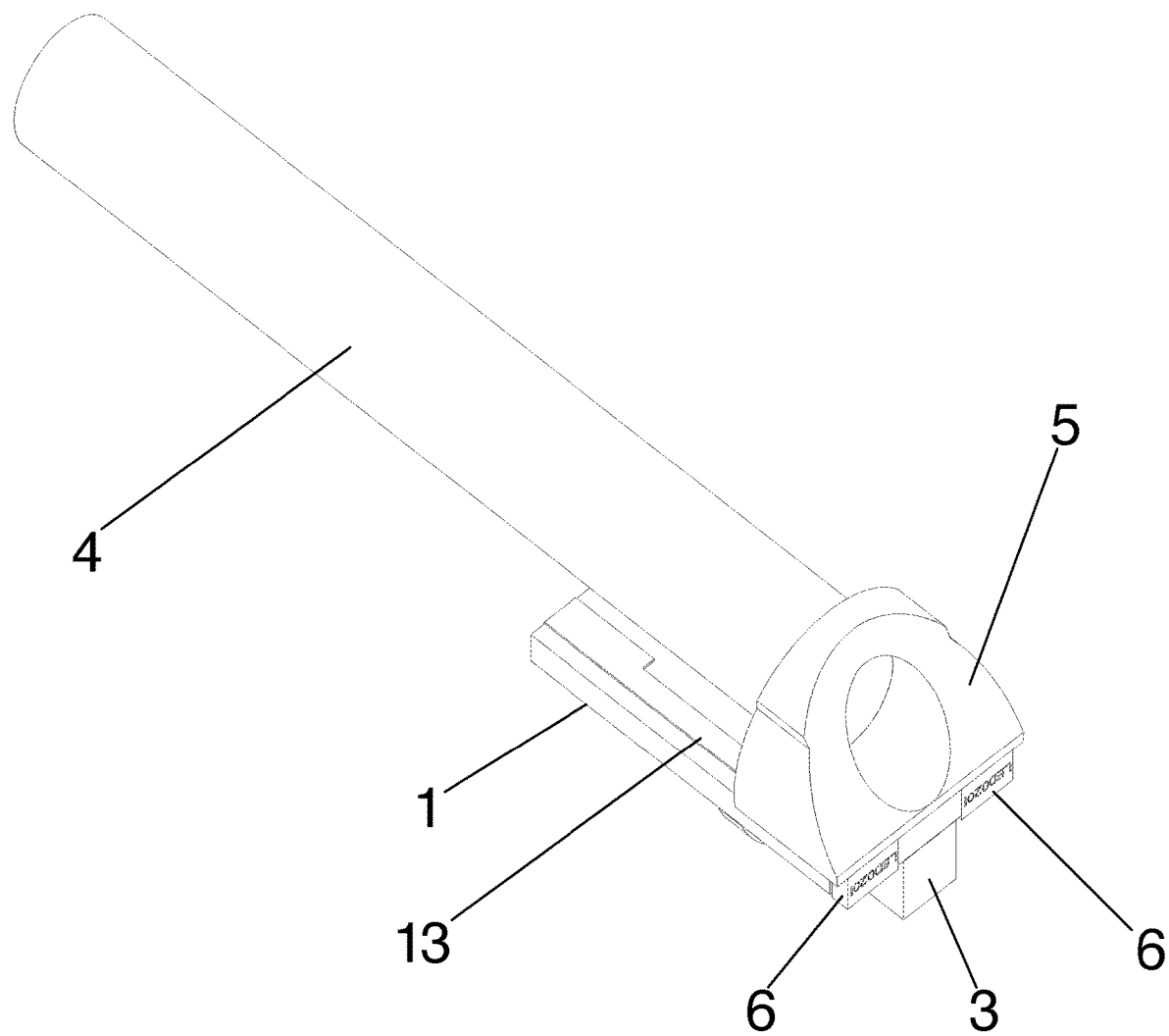
FIG. 2 is a schematic structural diagram 2 of a part of a detection packaging structure based on a flexible tube except an outer tube according to an embodiment of the present invention.

FIG. 1 is a schematic structural diagram 1 of a part of a detection packaging structure based on a flexible tube except an outer tube according to an embodiment of the present invention. FIG. 2 is a schematic structural diagram 2 of a part of a detection packaging structure based on a flexible tube except an outer tube according to an embodiment of the present invention.

Referring to FIG. 1, the detection packaging structure based on the flexible tube includes: a main circuit board 1, a detection circuit board 2, a detection component 3, an instrument tube 4, a tube cap 5, and an outer tube 7.

The detection circuit board 2 is perpendicularly disposed on a first side surface, along a first direction, of the main circuit board 1, and the instrument tube 4 is disposed on a second side surface, along the first direction, of the main circuit board. The tube cap 5 is mounted on the second side surface of the main circuit board, and is connected to an end of the instrument tube.

The first direction may be understood as a direction of a front side/reverse side, or may be understood as a direction perpendicular to a surface of the main circuit board 1. In this way, the detection circuit board 2 and the instrument tube 4 may be respectively disposed on surfaces on two sides of the main circuit board 1.

The detection component 3 is disposed, along the second direction, on a first side surface of the detection circuit board 2.

The second direction may be understood as a direction of a front side/reverse side of the detection circuit board 2, or may be understood as a direction perpendicular to a surface of the detection circuit board 2, or may be understood as a length direction of the instrument tube 4. The first side surface of the detection circuit board 2 may face a detection direction, so that the detection component 3 may face the detection direction. The first direction and the second direction may be understood as directions perpendicular to each other.

It may be seen that, based on this embodiment, stable mounting and use of the detection component are further ensured through assembly of the main circuit board and the detection circuit board, so that the detection component is not impacted by external force. In addition, the detection circuit board is perpendicularly disposed on the first side surface of the main circuit board, which helps rationalize space utilization, thereby facilitating reduction of an overall size of the structure.

A first conducting material (not shown in the figure) is disposed on the first side surface, along the second direction, of the detection circuit board 2, a second conducting material 21 capable of being conducted to the first conducting material is disposed on a second side surface, along the second direction, of the detection circuit board 2, a detection conducting material 11 is disposed on the first side surface of the main circuit board 1, a wiring terminal of the detection component 3 is conductively connected to the first conducting material, one end of the detection conducting material 11 is conductively welded to the second conducting material 21, and the other end of the detection conducting material 11 is conductively connected to a cable.

It may be seen that, in this embodiment, the cable is prevented from being directly welded to the detection component by using the main circuit board and the detection circuit board that are perpendicular to each other, and the conducting materials disposed on the detection circuit board. In addition, the detection component needs to be welded only to the first conducting material disposed on the first side surface, thereby helping enlarge a welding spot of the detection component. Therefore, based on the present invention, difficulty of welding operations is reduced, welding strength and reliability are enhanced, and welding stability in a plurality of motion statuses is satisfied.

In addition, the first side surface and the second side surface of the main circuit board 1, and the first side surface and the second side surface of the detection circuit board 2 may all be planes, and an implementation in which these side surfaces are curved surfaces or arc-shaped surfaces is not excluded in this embodiment.

The first conducting material may be any material that can be connected and electrically conductive, and may be a metal sheet such as a copper sheet. In an implementation, the first conducting material may be disposed on the first side surface. In another optional implementation, a groove may be provided on the first side surface, so that the first conducting material may be disposed in the groove.

The second conducting material 21 may be any material that can be connected and electrically conductive, and may be a metal sheet such as a copper sheet. In an implementation, the second conducting material may be disposed on the second side surface. In another optional implementation, a groove may be provided on the first side surface, so that the second conducting material may be disposed in the groove.

The detection conducting material 11 may be any material that can be connected and electrically conductive, and is specifically conducted to the conducting material on the detection circuit board 2, so that signal and/or electric energy can be transmitted between the cable and the detection circuit board 2. The detection conducting material 11 may be a metal sheet such as a copper sheet. In an implementation, the detection conducting material 11 may extend to an outer end surface and/or an inner end surface of the main circuit board.

The instrument tube 4 may be understood as a tube that can be equipped with a biopsy instrument, a laser instrument, or the like, and may be flexible. For details, refer to definitions of the instrument tube 4 in a controllable curved tube in the field for understanding.

Figure 3:
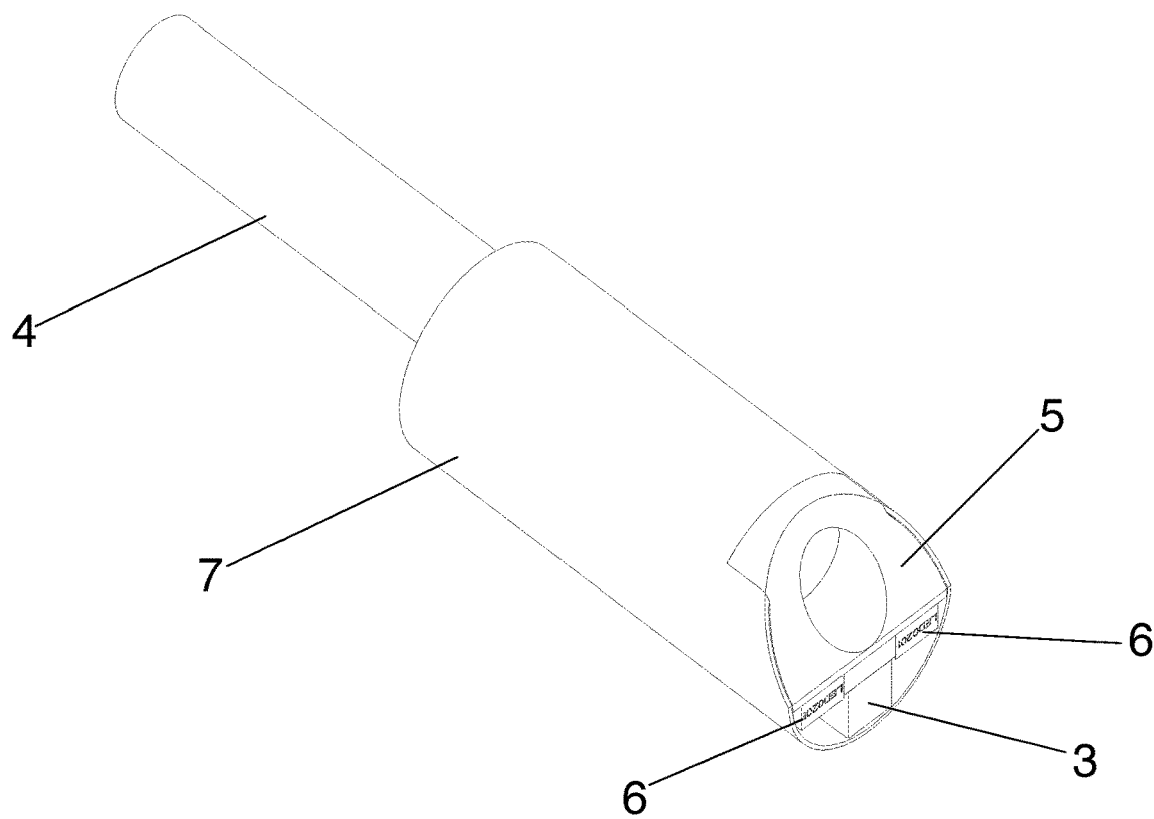
FIG. 3 is a schematic structural diagram 1 of a detection packaging structure based on a flexible tube according to an embodiment of the present invention.
Figure 4:
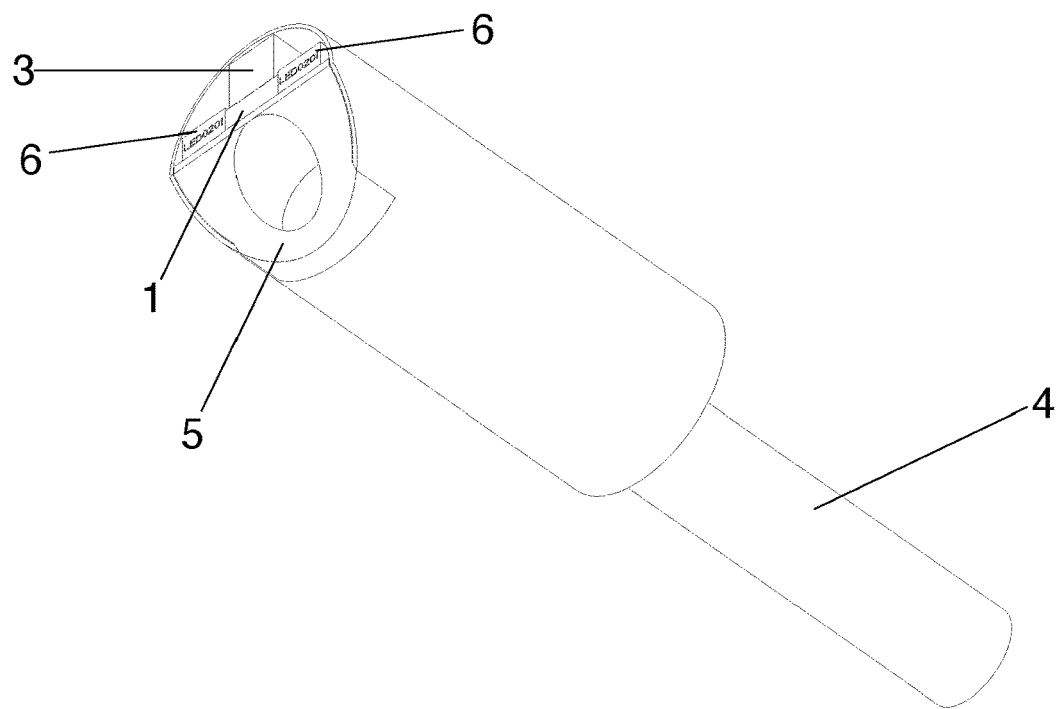
FIG. 4 is a schematic structural diagram 2 of a detection packaging structure based on a flexible tube according to an embodiment of the present invention.
Figure 5:
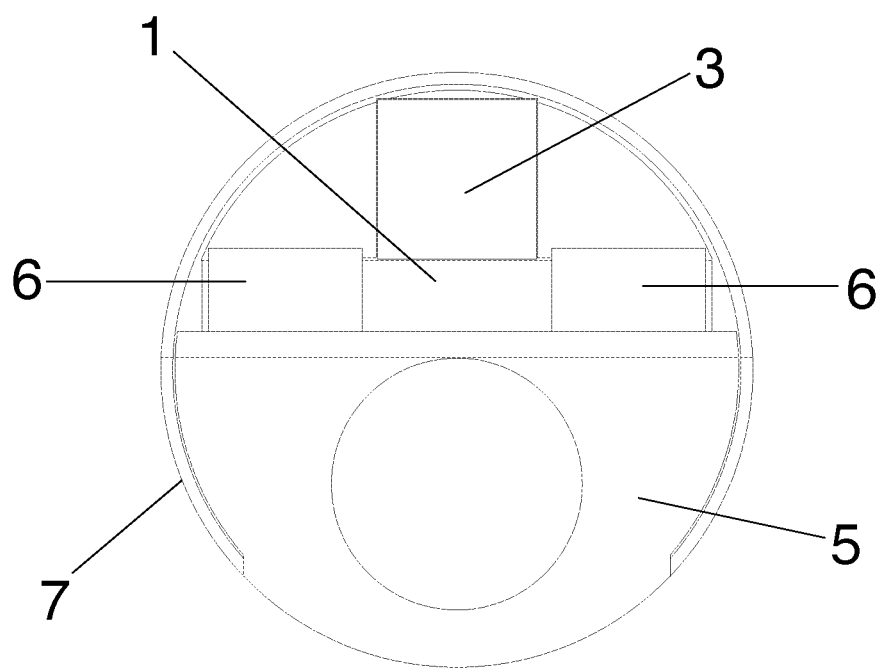
FIG. 5 is a schematic structural diagram of an end surface of a detection packaging structure based on a flexible tube according to an embodiment of the present invention.

FIG. 3 is a schematic structural diagram 1 of a detection packaging structure based on a flexible tube according to an embodiment of the present invention. FIG. 4 is a schematic structural diagram 2 of a detection packaging structure based on a flexible tube according to an embodiment of the present invention. FIG. 5 is a schematic structural diagram of an end surface of a detection packaging structure based on a flexible tube according to an embodiment of the present invention.

Referring to FIG. 3 to FIG. 5, in the embodiments, the main circuit board 1, the detection circuit board 2, the detection component 3, the tube cap 5, and a part of the instrument tube 4 are all disposed in the outer tube 7, and the outer tube 7 is directly or indirectly connected to a flexible controllable curved tube.

The outer tube 7 can be filled with glue, through which locations of the circuit boards, components, and instrument tube can be fixed, thereby implementing overall packaging of the apparatus. It may be understood that, the outer tube 7 being filled with glue means that as long as there is glue in the outer tube 7, the above description applies regardless of whether all empty spaces are filled.

An integral insertion portion may be formed through fixing by using glue.

Figure 6:
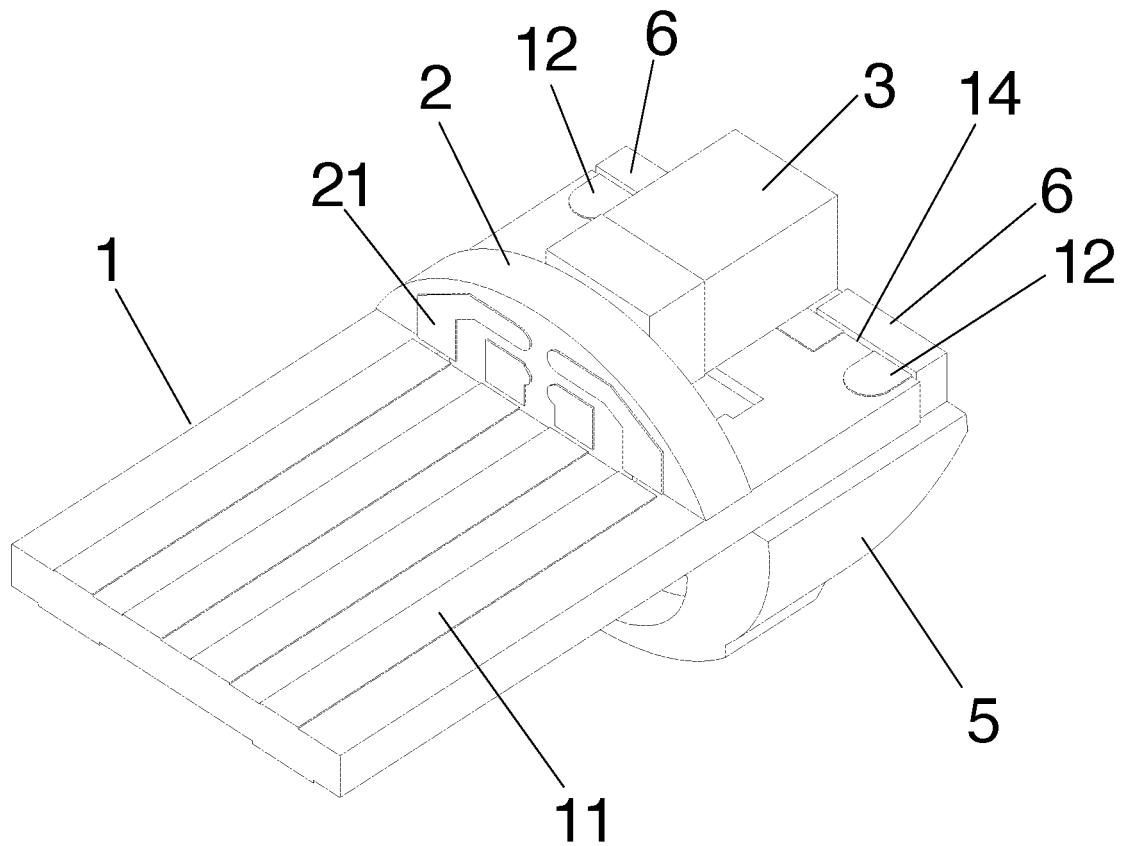
FIG. 6 is a schematic structural diagram 1 of a part of a detection packaging structure based on a flexible tube except an outer tube and an instrument tube according to an embodiment of the present invention.
Figure 7:
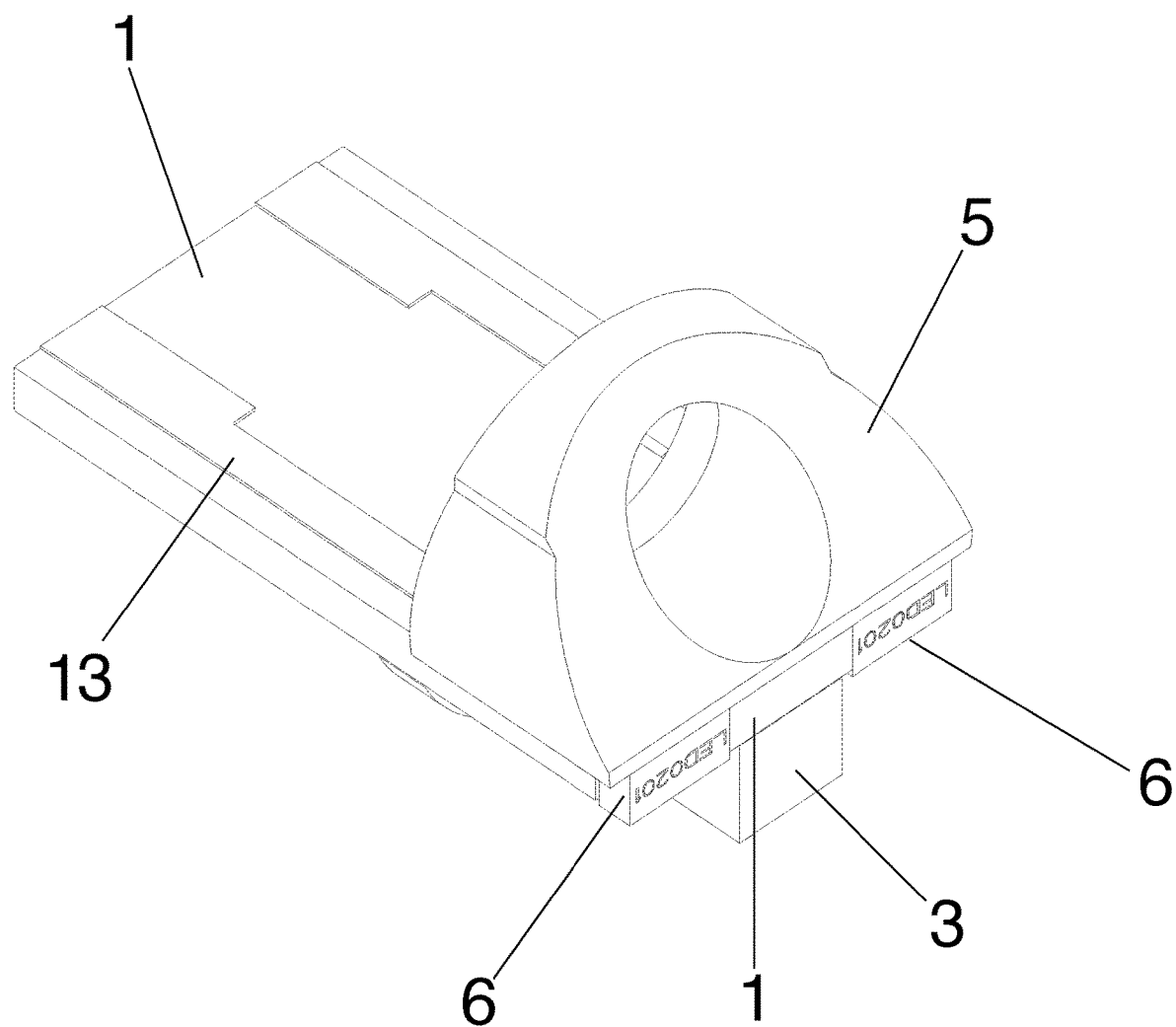
FIG. 7 is a schematic structural diagram 2 of a part of a detection packaging structure based on a flexible tube except an outer tube and an instrument tube according to an embodiment of the present invention.
Figure 8:
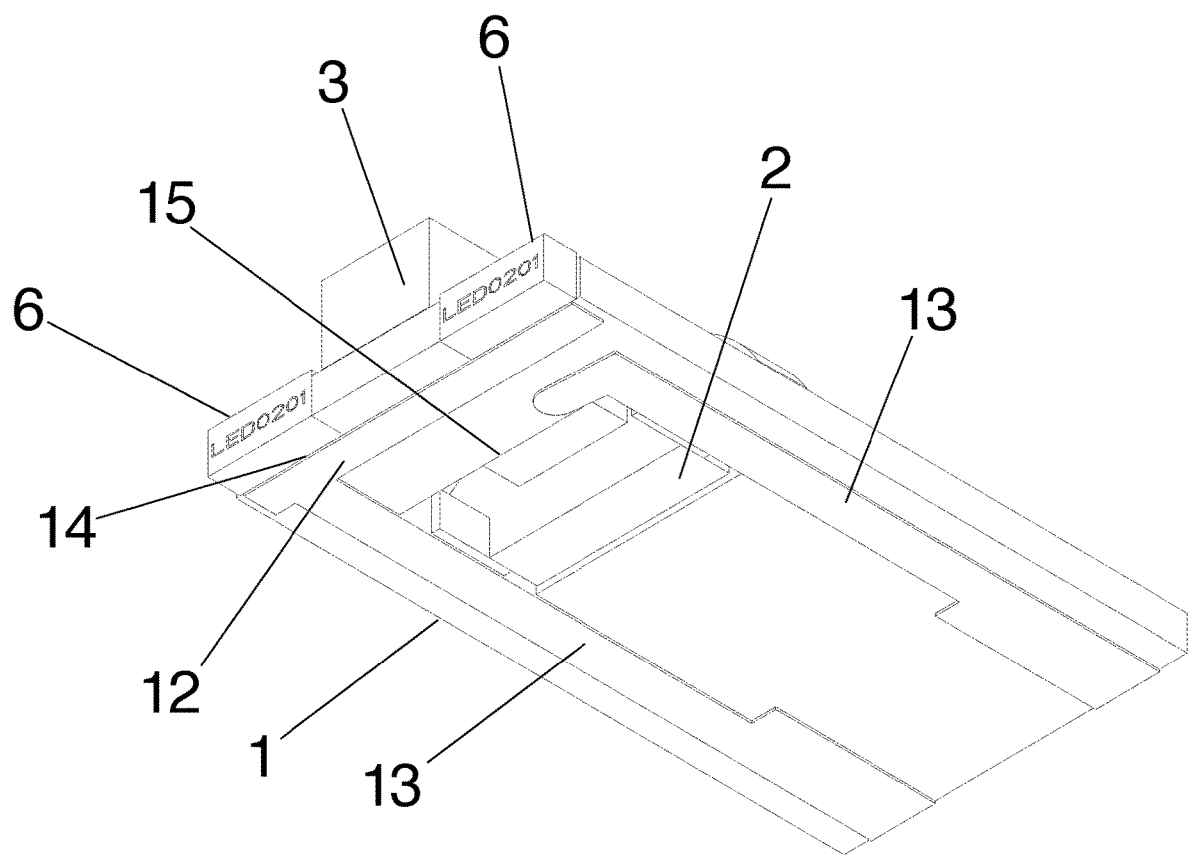
FIG. 8 is a schematic structural diagram 3 of a part of a detection packaging structure based on a flexible tube except an outer tube and an instrument tube according to an embodiment of the present invention, where

FIG. 6 is a schematic structural diagram 1 of a part of a detection packaging structure based on a flexible tube except an outer tube and an instrument tube according to an embodiment of the present invention. FIG. 7 is a schematic structural diagram 2 of a part of a detection packaging structure based on a flexible tube except an outer tube and an instrument tube according to an embodiment of the present invention. FIG. 8 is a schematic structural diagram 3 of a part of a detection packaging structure based on a flexible tube except an outer tube and an instrument tube according to an embodiment of the present invention.

Referring to FIG. 1 to FIG. 6, in an implementation, the detection conducting material 11 includes at least two conductive portions, the conductive portions are along the second direction, and the at least two conductive portions are parallel to each other. The conductive portion is rectangular and can directly conduct the cable and the second conducting material at two ends.

It may be seen that the conductive portions are lined up and arranged in parallel, which can facilitate welding between the detection conducting material 11 and the cable, and can effectively increase welding strength.

In an implementation, referring to FIG. 8, with reference to other accompanying drawings, the main circuit board 1 is provided with a mounting locating groove 15, and both the detection circuit board 2 and the tube cap 5 are mounted in the mounting locating groove 15 in an insertion manner.

The mounting locating groove 15 is provided, so that the detection circuit board 2 and the tube cap 5 can be mounted in an insertion manner. Therefore, a radial size of an overall structure can be effectively controlled through rational utilization of space.

The mounting locating groove 15 may be a rectangular groove. The tube cap 5 may be mounted on a part, distal from the cable, of the mounting locating groove 15 along the second direction. The detection circuit board 2 may be mounted on a part, proximal to the cable, of the mounting locating groove 15 along the second direction.

While mounting and locating are performed, a connecting component may be further disposed on an edge of the mounting locating groove 15. For example, the connecting component may be any connecting component used for gluing, clamping, and welding, which can further facilitate stabilization of mounting and locating between the main circuit board 1 and the detection circuit board 2, and stabilization of mounting and locating between the main circuit board 1 and the tube cap 5.

In an implementation, an edge of a side, distal from the main circuit board 1, of the detection circuit board 2 is arc-shaped, and the arc-shaped edge matches an inner surface of the outer tube 7, so that the detection circuit board 2 and the outer tube 7 may be assembled on the edge.

In a specific implementation process, the detection circuit board 2 may include a semicircular portion, and an insertion portion disposed on a linear edge of the semicircular portion along the first direction. The insertion portion may be inserted into the mounting locating groove 15, and the semicircular portion is along a third direction perpendicular to the first direction and the second direction. A diameter of the semicircular portion needs to be greater than a size of the insertion portion along the third direction, and the size of the insertion portion along the third direction matches a size of the mounting locating groove 15 along the third direction.

In a specific implementation process, an insertion portion is also disposed on a side, along the first direction, of the tube cap 5, and the insertion portion may be inserted into the mounting locating groove 15.

In an implementation, referring to FIG. 2, FIG. 3, FIG. 4, and FIG. 7, an end surface of an end, distal from the instrument tube, of the tube cap 5 is provided with a first inclined surface, and an end surface, proximal to the tube cap, of the outer tube 7 is provided with a second inclined surface whose angle matches an angle of the first inclined surface.

It may be understood that an axis of the instrument tube 4 and each of the first inclined surface and the second inclined surface can form a non-right included angle. It may be understood that, the angle of the first inclined surface matching the angle of the second inclined surface means that the included angle between the first inclined surface and the axis and the included angle between the second inclined surface and the axis are the same or a difference between the included angles is less than a threshold. In addition, the first inclined surface may be a part of the end surface of the tube cap 5, or may be all of the end surface of the tube cap 5. The second inclined surface may be a part of the end surface of the outer tube 7, or may be all of the end surface of the outer tube 7.

In addition, the foregoing inclined surfaces may be flat inclined surfaces or may be curved.

Insertion passability of the structure or the formed insertion portion may be effectively improved by using the first inclined surface of the tube cap 5 and the second inclined surface of the outer tube 7.

In an implementation, the detection component 3 may be an image acquisition component. In another optional implementation, the detection component 3 may also be any detection apparatus that detects physical and chemical properties of a liquid, a gas, or a solid, such as a liquid detection component or a gas detection component.

The detection component 3 may be the image acquisition component. With quick development of image sensors, the smallest image sensor can now achieve 0.7*0.7 mm. Therefore, there is an urgent need for a packaging structure that can effectively control an external diameter and be safely and reliably packaged with lighting and low costs. However, the apparatus in this embodiment can exactly meet this demand.

To be suitable for implementing effective image acquisition, the apparatus may further include a lighting component 6. Specifically, the lighting component 6 is disposed at an end of the main circuit board 1, which can also be understood as that the lighting component 6 is disposed at an end, proximal to the detection component 3, of the main circuit board 1. Both the lighting component 6 and the detection component 3 are along the second direction, and face a same direction. The same direction may be a detection direction, in other words, a lighting direction.

In a specific implementation process, a quantity of lighting components 6 may be two groups, and the light components 6 are distributed at the end of the main circuit board 1 along the third direction. In addition, the two groups of lighting components 6 may be uniformly distributed on two sides of the detection component 3 along the third direction, thereby facilitating implementation of clear and uniform lighting.

The lighting component 6 may be any component that can emit light, or may be any component with any color and any lighting principle. For example, the lighting component 6 may be an LED. In a specific implementation process, the lighting component 6 may be monochromatic, multicolor, or allochroic.

In an implementation, referring to FIG. 6 and FIG. 8, an opening groove 14 is provided at the end of the main circuit board 1, and the lighting component 6 is disposed in the opening groove 14. A shape of the opening groove 14 may match an external shape of the lighting component 6.

It may be seen that the opening groove 14 may facilitate stable mounting of the lighting component 6.

In addition, a depth of the opening groove 14 along the second direction may be associated with a size of the detection component 3 along the second direction, which can help ensure that an end, distal from the detection circuit board 2, of the detection component 3 and an end, distal from the detection circuit board 2, of the lighting component 6 stay in a same reference plane. The reference plane is a plane perpendicular to the second direction. In addition, the end of the lighting component 5 may also be slightly higher or lower than the end of the detection component 3 along the second direction. The two ends conform to the matching described above, and are also located in a same reference plane described above.

It may be seen that the lighting component 6 and the detection component 3 being in the same reference plane can make lighting more uniform.

The lighting conducting material and the cable to which the lighting conducting material is connected may transmit signals or electric energy.

In an implementation, a lighting conducting material is further disposed on the first side surface and/or the second side surface of the main circuit board 1, the lighting conducting material is conductively welded to the lighting component 6, at least two lighting components are connected in parallel, and the lighting conducting material is conductively connected to the cable.

The lighting conducting material may include a first lighting conducting material 12 conductively welded to the lighting component 6, and a second lighting conducting material 13 conductively welded to the first lighting conducting material 12 and the cable along the second direction. The second lighting conducting material 13 may be similar to the detection conducting material 11, and includes conductive portions parallel to each other. In addition, the conductive portions may be lined up and arranged in parallel, which can facilitate welding between the second lighting conducting material 13 and the cable, and can effectively increase welding strength.

It may be seen that, by using the circuit boards and the conducting materials, welding strength and reliability of the detection component, the lighting component, and the cable can be effectively improved, and a short circuit risk between a welding spot and the outer tube can be reduced.

In addition, a cable corresponding to lighting and a cable corresponding to detection may be different cables or may be disposed in a same cable.

In a specific implementation process, the cable may be a coaxial cable with a shielding layer. The shielding layer can effectively enhance welding strength and avoid occurrence of an abnormality in the cable.

In an implementation, the instrument tube 4 and the tube cap 5 may be glued together, and the detection component 3 and the main circuit board 1 may also be glued together. Therefore, stability of locations between each other can be ensured, and a glue filling manner is also not excluded in this implementation.

The structure provided in the foregoing solutions has the following positive effects: an ingenious design, less parts, rational utilization of space, simplicity, reliability, and being easy to manufacture. In addition, if this embodiment and the optional solutions of this embodiment are applied to the endoscope field, an insertion portion, with an inclined edge and a diameter of less than 3 mm, of a micro sensor endoscope can be obtained through packaging, which greatly expands an application range of micro sensors in the endoscope field.

This embodiment further provides an in-vivo detection apparatus based on a flexible tube, including the detection packaging structure based on the flexible tube and the flexible controllable curved tube in the foregoing optional solutions, where the detection packaging structure based on the flexible tube forms an insertion portion at an end of the controllable curved tube.

The insertion portion and the controllable curved tube may be a controllable curved tube and an insertion portion of an endoscope.

To sum up, for the detection packaging structure and the in-vivo detection apparatus that are based on the flexible tube provided in this embodiment, the detection circuit board and the main circuit board that are perpendicular to each other are used, the first conducting material is disposed on the first side surface of the detection circuit board, the second conducting material capable of being conducted to the first conducting material is disposed on the second side surface, and when the detection component is connected to the first side surface of the detection circuit board, the wiring terminal of the detection component is capable of being welded to the first conducting material. In this way, the cable is prevented from being directly welded to the detection component by using the main circuit board and the detection circuit board that are perpendicular to each other, and the conducting materials disposed on the detection circuit board. In addition, the detection component needs to be welded only to the first conducting material disposed on the first side surface, thereby helping enlarge a welding spot of the detection component. Therefore, based on the present invention, difficulty of welding operations is reduced, welding strength and reliability are enhanced, and welding stability in a plurality of motion statuses is satisfied.

Based on this embodiment, stable mounting and use of the detection component are further ensured through assembly of the main circuit board and the detection circuit board, so that the detection component is not impacted by external force. In addition, the detection circuit board is perpendicularly disposed on the first side surface of the main circuit board, which helps rationalize space utilization, thereby facilitating reduction of an overall size of the structure.

At last, it should be noted that the above various embodiments are only used to describe the technical solutions of the present invention, rather than limiting the technical solutions of the present invention. Even through the present invention is described in detail with reference to the foregoing embodiments, those of ordinary skilled in the art should understand that they can still modify the technical solutions recorded in the foregoing various embodiments or equivalently replace some or all of the technical features. However, these modifications or replacements do not make the essence of the corresponding technical solutions deviate from the scope of the technical solutions of the embodiments of the present invention.

What is claimed is:

1. An in-vivo detection apparatus based on a flexible tube, comprising
    a detection packaging structure based on the flexible tube comprising:
        a main circuit board, a detection circuit board, a detection component, an instrument tube, a tube cap, and an outer tube, wherein
        the detection circuit board is perpendicularly disposed on a first side surface, along a first direction, of the main circuit board, the instrument tube is disposed on a second side surface, along the first direction, of the main circuit board, and the detection component is disposed, along a second direction, on a first side surface of the detection circuit board; the tube cap is mounted on the second side surface of the main circuit board, and is connected to an end of the instrument tube;
        a first conducting material is disposed on the first side surface, along the second direction, of the detection circuit board, a second conducting material capable of being conducted to the first conducting material is disposed on a second side surface, along the second direction, of the detection circuit board, a third conducting material is disposed on the first side surface of the main circuit board, a wiring terminal of the detection component is conductively welded to the first conducting material, one end of the detection conducting material is conductively welded to the second conducting material, and the other end of the detection conducting material is conductively connected to a cable;

the main circuit board, the detection circuit board, the detection component, the tube cap, and a part of the instrument tube are all disposed in the outer tube, and the outer tube is directly or indirectly connected to a flexible controllable curved tube; and the first direction is perpendicular to the second direction, wherein the detection packaging structure based on the flexible tube forms an insertion portion at an end of the controllable curved tube, wherein the main circuit board is provided with a mounting locating groove, and both the detection circuit board and the tube cap are mounted in the mounting locating groove in an insertion manner.

2. The in-vivo detection apparatus based on a flexible tube according to claim 1, wherein the detection conducting material comprises at least two conductive portions, the conductive portions are along the second direction, and the at least two conductive portions are parallel to each other.

3. The in-vivo detection apparatus based on a flexible tube according to claim 2, wherein the detection component is an image acquisition component; a lighting component is disposed at an end of the main circuit board, and both the lighting component and the detection component are along the second direction, and face a same direction.

4. The in-vivo detection apparatus based on a flexible tube according to claim 2, wherein the instrument tube and the tube cap are glued together, and the detection component and the main circuit board are glued together.

5. The in-vivo detection apparatus based on a flexible tube according to claim 2, wherein an edge of a side, distal from the main circuit board, of the detection circuit board is arc-shaped, and the arc-shaped edge matches an inner surface of the outer tube.

6. The in-vivo detection apparatus based on a flexible tube according to claim 1, wherein an end surface of an end, distal from the instrument tube, of the tube cap is provided with a first inclined surface, and an end surface, proximal to the tube cap, of the outer tube is provided with a second inclined surface whose angle matches an angle of the first inclined surface.

7. The in-vivo detection apparatus based on a flexible tube according to claim 6, wherein the detection component is an image acquisition component; a lighting component is disposed at an end of the main circuit board, and both the lighting component and the detection component are along the second direction, and face a same direction.

8. The in-vivo detection apparatus based on a flexible tube according to claim 6, wherein the instrument tube and the tube cap are glued together, and the detection component and the main circuit board are glued together.

9. The in-vivo detection apparatus based on a flexible tube according to claim 6, wherein an edge of a side, distal from the main circuit board, of the detection circuit board is arc-shaped, and the arc-shaped edge matches an inner surface of the outer tube.

10. The in-vivo detection apparatus based on a flexible tube according to claim 1, wherein the detection component is an image acquisition component; a lighting component is disposed at an end of the main circuit board, and both the lighting component and the detection component are along the second direction, and face a same direction.

11. The in-vivo detection apparatus based on a flexible tube according to claim 10, wherein an opening groove is provided at the end of the main circuit board, and the lighting component is disposed in the opening groove.

12. The in-vivo detection apparatus based on a flexible tube according to claim 1, wherein a lighting conducting material is further disposed on the first side surface and/or the second side surface of the main circuit board, the lighting conducting material is conductively welded to a lighting component, wherein the lighting component comprises at least two lighting components connected in parallel, and the lighting conducting material is conductively connected to the cable.

13. The in-vivo detection apparatus based on a flexible tube according to claim 1, wherein the instrument tube and the tube cap are glued together, and the detection component and the main circuit board are glued together.

14. The in-vivo detection apparatus based on a flexible tube according to claim 1, wherein an edge of a side, distal from the main circuit board, of the detection circuit board is arc-shaped, and the arc-shaped edge matches an inner surface of the outer tube.

15. The in-vivo detection apparatus based on a flexible tube according to claim 1, wherein the detection component is an image acquisition component; a lighting component is disposed at an end of the main circuit board, and both the lighting component and the detection component are along the second direction, and face a same direction.

16. The in-vivo detection apparatus based on a flexible tube according to claim 1, wherein the instrument tube and the tube cap are glued together, and the detection component and the main circuit board are glued together.

17. The in-vivo detection apparatus based on a flexible tube according to claim 1, wherein an edge of a side, distal from the main circuit board, of the detection circuit board is arc-shaped, and the arc-shaped edge matches an inner surface of the outer tube.

18. An in-vivo detection apparatus based on a flexible tube, comprising a detection packaging structure based on the flexible tube comprising:

a main circuit board, a detection circuit board, a detection component, an instrument tube, a tube cap, and an outer tube, wherein the detection circuit board is perpendicularly disposed on a first side surface, along a first direction, of the main circuit board, the instrument tube is disposed on a second side surface, along the first direction, of the main circuit board, and the detection component is disposed, along a second direction, on a first side surface of the detection circuit board; the tube cap is mounted on the second side surface of the main circuit board, and is connected to an end of the instrument tube;

a first conducting material is disposed on the first side surface, along the second direction, of the detection circuit board, a second conducting material capable of being conducted to the first conducting material is disposed on a second side surface, along the second direction, of the detection circuit board, a detection conducting material is disposed on the first side surface of the main circuit board, a wiring terminal of the detection component is conductively welded to the first conducting material, one end of the detection conducting material is conductively welded to the second conducting material, and the other end of the detection conducting material is conductively connected to a cable;

the main circuit board, the detection circuit board, the detection component, the tube cap, and a part of the instrument tube are all disposed in the outer tube, and the outer tube is directly or indirectly connected to a flexible controllable curved tube; and the first direction is perpendicular to the second direction, wherein the detection packaging structure based on the flexible tube forms an insertion portion at an end of the controllable curved tube, wherein the detection component is an image acquisition component; a lighting component is disposed at an end of the main circuit board, and both the lighting component and the detection component are along the second direction, and face a same direction, wherein an opening groove is provided at the end of the main circuit board, and the lighting component is disposed in the opening groove.

* * * * *